US00PP31023P3

(12) United States Plant Patent
Heimovaara

(10) Patent No.: US PP31,023 P3
(45) Date of Patent: Nov. 5, 2019

(54) ***CHRYSANTHEMUM* PLANT NAMED 'ZANMUPOP ORANGE'**

(50) Latin Name: ***Chrysanthemum* x *morifolium* Ramat.**
Varietal Denomination: Zanmupop Orange

(71) Applicant: Van Zanten Breeding BV, Aalsmeer (NL)

(72) Inventor: Sjoukje Heimovaara, Valkenburg (NL)

(73) Assignee: VAN ZANTEN BREEDING BV (NL)

( * ) Notice: Subject to any disclaimer, the term of this patent is extended or adjusted under 35 U.S.C. 154(b) by 0 days.

(21) Appl. No.: 15/732,814

(22) Filed: Jan. 4, 2018

(65) Prior Publication Data

US 2019/0208682 P1 Jul. 4, 2019

(51) Int. Cl.
*A01H 5/02* (2018.01)
*A01H 6/14* (2018.01)

(52) U.S. Cl.
USPC ..... Plt./296
CPC ..... *A01H 6/1424* (2018.05)

(58) Field of Classification Search
USPC ..... Plt./296
CPC ..... A01H 5/02; A01H 6/1424
See application file for complete search history.

*Primary Examiner* — Keith O. Robinson
(74) *Attorney, Agent, or Firm* — Steptoe & Johnson LLP

(57) ABSTRACT

A *chrysanthemum* plant named 'Zanmupop Orange' characterized by its medium sized blooms with light bronze ray florets and a dark rim the center, and prolific branching; natural season flowering date October 2; blooming for a period of 5 weeks.

3 Drawing Sheets

Botanical designation: *Chrysanthemum* x *morifolium* Ramat.

Cultivar denomination: 'Zanmupop Orange'.

RELATED CULTIVARS

The new plant is a flower color mutant of 'Zanmupop' (U.S. Plant Pat. No. 28,942)

BACKGROUND OF THE INVENTION

The present invention relates to a new and distinct cultivar of *chrysanthemum* plant, botanically known as *Chrysanthemum* x *morifolium* Ramat., commercially known as a garden mum, and hereinafter referred to by the cultivar denomination 'Zanmupop Orange'. 'Zanmupop Orange' is a product of a breeding and selection program which had the objective of finding flower color mutants from existing parent plants. The new plant comprises a whole plant mutant of the parent *chrysanthemum* named 'Zanmupop' (U.S. Plant Pat. No. 28,942). A comparison between the parent and the flower color mutant is provided in the section description of the invention.

Plants from the new cultivar 'Zanmupop Orange' differ from plants of the parent in the color of the ray florets. The ray florets of the parent are pink, while those of the new plant are bronze.

In order to obtain color mutants, unrooted cuttings of the parent plant were irradiated in April 2013 at Ziekenhuis, Rotterdam, the Netherlands, with gamma radiation at a dose of 15Gy. These treated cuttings were then planted in a controlled environment (greenhouse) in Rijsenhout, the Netherlands. In this population of planted cuttings, the new cultivar was discovered as a flower color mutant in October 2013 by Sjoukje Heimovaara. The first act of asexual reproduction of 'Zanmupop Orange' was accomplished when after planting of 'Zanmupop Orange' as a motherplant in December 2013, vegetative cuttings from 'Zanmupop Orange' were taken and propagated further in Rijsenhout, the Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *chrysanthemum* (of about 19 weeks) is shown in the accompanying drawings, the color being as nearly true as possible with color photographs of this type.

DESCRIPTION OF THE INVENTION

Figure 1:
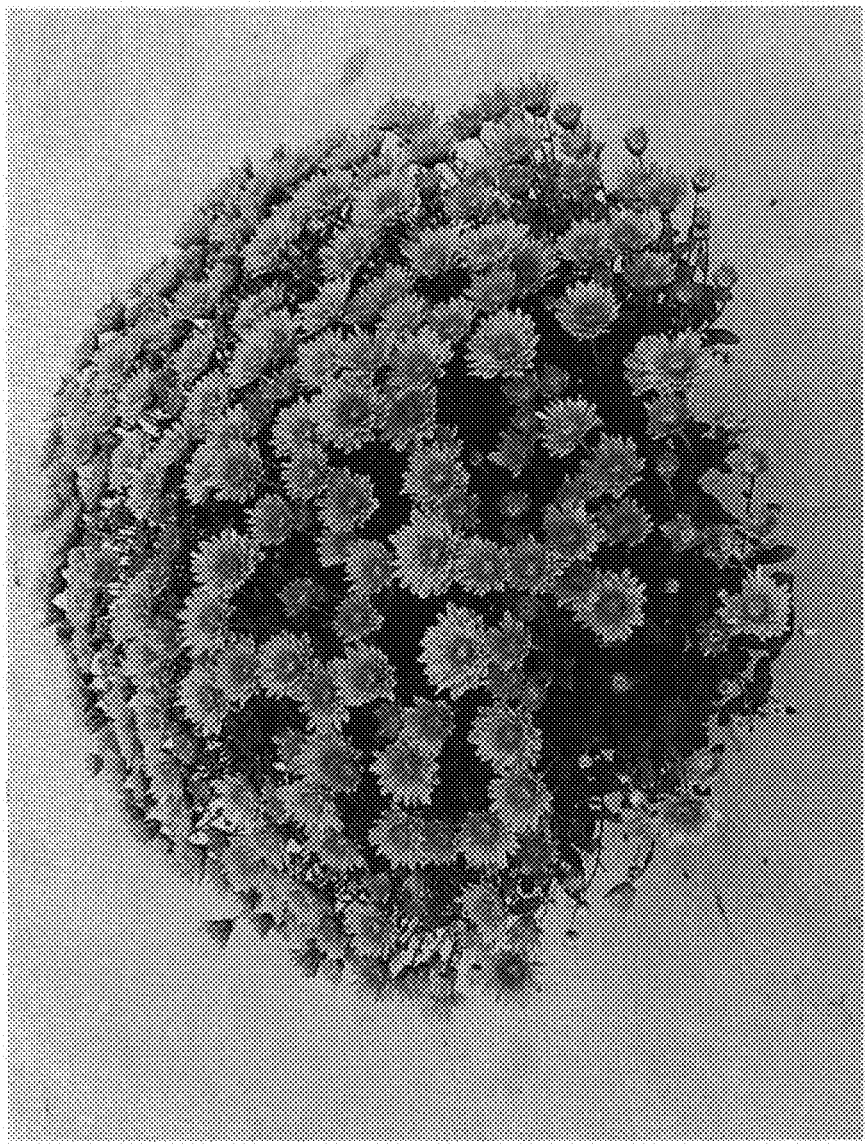
FIG. 1 shows a plant of the cultivar in full bloom.
Figure 2:
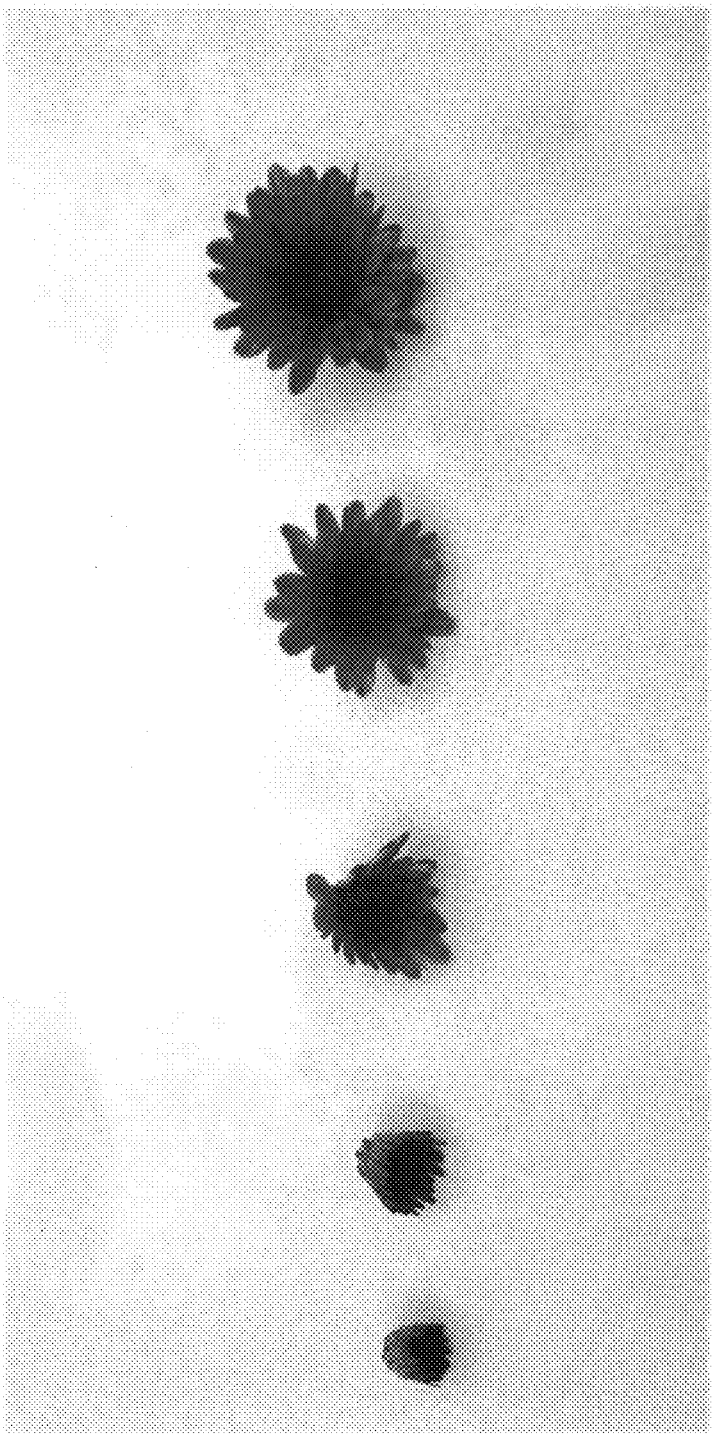
FIG. 2 shows the various stages of blooms of the new cultivar.
Figure 3:
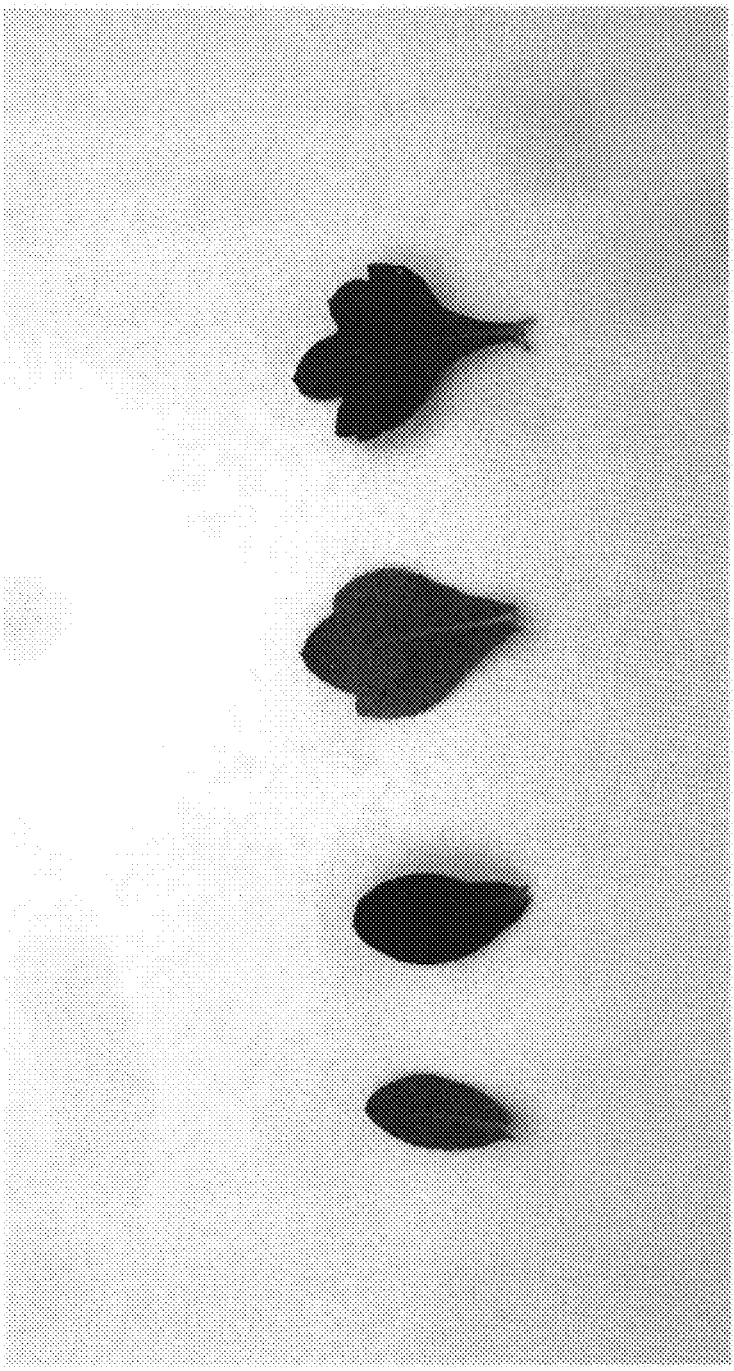
FIG. 3 shows the various stages of foliage of the new cultivar.

The observations and measurements were gathered from plants in the period of 16 to 23 weeks of age grown outdoor in Rijsenhout, the Netherlands, under natural day length and temperature and planted in week 23. The natural blooming date of this crop was October 2 (week 40). The average height of the plants was 30-35 cm. No growth retardants were used. No tests were done on disease or insects resistance or susceptibility. No tests were done on cold or drought resistance. This new variety produces medium sized blooms with light bronze ray florets and a dark rim in the center blooming for a period of five weeks.

From the cultivars known to the inventor the most similar existing cultivar in comparison to 'Zanmupop Orange' is its parent 'Zanmupop' and 'Zanmucopper' (U.S. Plant Pat. No. 29,449). When 'Zanmupop' and the two most similar varieties are being compared the following differences are noticed: (1) Ray floret color, and (2) Natural season blooming date. (1) Ray florets of 'Zanmupop' are pink, while those of 'Zanmupop Orange' and 'Zanmucopper' are bronze. (2) Plants of 'Zanmucopper' flower earlier in the season than those of 'Zanmupop' and 'Zanmupop Orange'.

The following is a description of the plant and characteristics that distinguish 'Zanmupop Orange' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour chart, sixth edition (2015).

Botanical Description of *Chrysanthemum* x *morifolium* Ramat. 'Zanmupop Orange'

Bud:
- *Size*.—Small; cross-section 3 mm, height 6 mm.
- *Shape*.—Round.
- *Texture*.—Pubescent.
- *Outside color*.—Greyed-green 191B.

Phyllaries:
- *Number*.—24, arranged in 3 rows.
- *Shape*.—Elliptic.
- *Apex*.—Acute.
- *Base*.—Truncate.
- *Margin*.—Entire.
- *Color*.—Upper side: Green 143C. Lower side: Greyed-green 191B.
- *Length and width*.—4 mm; 1.5 mm.
- *Texture*.—Pubescent.

Inflorescences:
- *Type*.—Double.
- *Height*.—1.3 cm.
- *Diameter*.—4 cm.
- *Peduncle length*.—5-6.5 cm.
- *Peduncle color*.—Green 138B.
- *Peduncle diameter*.—1.5 mm.
- *Peduncle texture*.—Pubescent.
- *Number per branch*.—About 7 inflorescences.
- *Duration of flowering*.—5 weeks.
- *Seeds*.—Produced in small quantities, ovate, Greyed-brown 199A, length 1.5 mm, diameter 0.5 mm; texture: rough with ribs.
- *Fragrance*.—Faint *chrysanthemum* odor.

Color inflorescences:
- *Center of inflorescence* (*disc florets*).—Immature stage: Green-yellow 1D ; Mature stage: Yellow 12A.
- *Color of upper side of ray florets*.—Outer rows: Greyed-orange 167B; Inner Rows: Greyed-purple 183B.
- *Color of lower side of ray florets*.—Outer rows: Greyed-orange 160D overlain with Greyed-purple 183D; Inner Rows: Greyed-purple 182A.
- *Tonality from distance*.—A garden mum with light bronze blooms and a dark rim in the center.
- *Color of ray florets after aging of the plant*.—Greyed-orange 167D.

Ray florets:
- *Number of types*.—2.
- *Type*.—Outer rows: Ligulate; Inner rows: Quilled.
- *Rows*.—10-12.
- *Texture*.—Upper and lower side smooth.
- *Number*.—160-170.
- *Density*.—Medium.
- *Shape*.—Outer rows: Elliptic; Inner rows: Narrowly elliptic.
- *Apex*.—Outer rows: Dentate; Inner rows: Rounded.
- *Base*.—Attenuate.
- *Cross-section*.—Outer rows: Flat; Inner rows: Circular.
- *Longitudinal axis*.—Outer rows: Straight; Inner rows: Incurving.
- *Length of corolla tube* (*outer rows*).—3 mm.
- *Diameter corolla tube* (*outer rows*).—1 mm.
- *Ray floret margin*.—Entire.
- *Ray floret length*.—Outer rows: 2.5 cm: Inner rows: 1.2 cm.
- *Ray floret width*.—Outer rows: 4 mm; Inner rows: 1.5 mm.
- *Ratio length/width*.—Medium (outer rows) to high (inner rows).

Disc florets:
- *Disc diameter*.—3-5 mm.
- *Number*.—About 40.
- *Shape*.—Tubular.
- *Color*.—Yellow-green 145C at base to Green Yellow 1D at apex.
- *Length*.—3 mm.
- *Diameter*.—1 mm.

Receptacle:
- *Color*.—Yellow-green 145D.
- *Shape*.—Domed raised.
- *Height*.—5 mm.
- *Diameter*.—7 mm.

Reproductive organs:
- *Androecium*.—Present in only disc florets.
- *Stamen length*.—3 mm.
- *Stamen color*.—Yellow-green 144A.
- *Anther color*.—Yellow 2A.
- *Pollen*.—Low amount.
- *Pollen color*.—Yellow 12A.
- *Gynoecium*.—Present in both ray and disc florets.
- *Style color*.—Yellow-green 154C.
- *Style length*.—4 mm.
- *Stigma color*.—Yellow 7A.
- *Stigma width*.—1 mm.
- *Ovary*.—Enclosed in calyx.
- *Ovary color*.—Yellow-green 149D.

Plant:
- *Type*.—Bushy.
- *Growth habit*.—Spherical shape.
- *Growth rate*.—Medium.
- *Height*.—30-35 cm.
- *Width*.—50 cm.
- *Stem color*.—Greyed-brown 199A.
- *Stem strength*.—Weak.
- *Stem brittleness*.—Brittle.
- *Stem anthocyanin coloration*.—Absent.
- *Internode length*.—1-3 cm.
- *Length of lateral branch*.—From top to bottom 22 cm.
- *Lateral branch color*.—Green 138A.
- *Lateral branch, attachment*.—Weak.
- *Lateral branch diameter*.—2 mm.
- *Lateral branch, texture*.—Pubescent with ribs.

*Branching* (*average number of lateral branches*).—Dense with 8-9 breaks after pinching.

*Natural season blooming date*.—October 2 (week 40) in Rijsenhout, the Netherlands.

*Roots*.—Habits: Fine, freely branching.

*Roots*.—Color: White 155A.

Foliage:

*Glossiness*.—Leaf upper side: very weak. Leaf lower side: absent.

*Leaf color*.—Upper side: Green 139A. Lower side: Green N138A.

*Color midvein*.—Upper side: Yellow-green 147D. Lower side: Yellow-green 148D.

*Size*.—Small; length 2.2-3 cm, width 1.5-2 cm.

*Quantity* (*number per lateral branches*).—22-24.

*Shape*.—Elliptic to widely elliptic.

*Texture upper side*.—parsely pubescent.

*Texture under side*.—Pubescent.

*Venation arrangement*.—Pinnate.

*Shape of margin*.—Serrated.

*Shape of base of sinus between lateral lobes*.—Rounded.

*Margin of sinus between lateral lobes*.—Diverging.

*Shape of base*.—Attenuate.

*Apex*.—Mucronulate.

*Petiole strength*.—Weak.

*Petiole attitude*.—Moderately upwards.

*Petiole length*.—0.2 cm.

*Petiole diameter*.—2 mm.

*Petiole color*.—Yellow-green 147D.

*Stipules*.—About 1-2 mm in size.

TABLE 1

Differences with the comparison varieties, when grown under identical conditions

| | 'Zanmupop Orange' | 'Zanmupop' | 'Zanmucopper' |
|---|---|---|---|
| Color upper side outer row ray florets | Greyed-orange 167B | Greyed-purple 186C to 186D | Greyed-orange 166C at base to Greyed-orange 163B at tip |
| Color upper side inner row ray florets | Greyed-purple 183B | Greyed-purple 186B | Greyed-orange 166A to 166B |
| Natural season blooming date | Week 40 | Week 41 | Week 38 |

I claim:

1. A new and distinct *chrysanthemum* plant named 'Zanmupop Orange' as described and illustrated.

* * * * *